United States Patent [19]

Ochi et al.

[11] Patent Number: 4,650,888

[45] Date of Patent: Mar. 17, 1987

[54] PENTAERYTHRITOL DERIVATIVE

[75] Inventors: Kiyoshige Ochi, Saitama; Yoshikazu Hinohara, Gunma; Isao Matsunaga, Tokyo, all of Japan

[73] Assignee: Chugai Seiyaku Kabushiki Kaisha, Tokyo, Japan

[21] Appl. No.: 721,850

[22] Filed: Apr. 10, 1985

[30] Foreign Application Priority Data

Apr. 18, 1984 [JP] Japan .................................. 59-76711

[51] Int. Cl.$^4$ .............................................. C07F 5/06
[52] U.S. Cl. ................................. 556/177; 556/182; 514/492
[58] Field of Search ................................. 556/177, 182

[56] References Cited

U.S. PATENT DOCUMENTS

| | | | |
|---|---|---|---|
| 2,155,961 | 4/1939 | Trowell | 556/177 |
| 2,168,660 | 8/1939 | Albrecht | 556/177 X |
| 2,760,970 | 8/1956 | Le Suer | 556/177 X |
| 3,150,161 | 9/1964 | Nunn | 556/177 X |
| 3,155,577 | 11/1964 | Mercer et al. | 556/177 X |
| 3,432,489 | 3/1969 | Nitta et al. | |
| 3,634,480 | 1/1972 | Sheffield | 556/177 X |
| 3,686,249 | 8/1972 | Hartmann | 556/182 X |
| 3,888,918 | 6/1975 | Kuehnhanss | 556/136 X |

FOREIGN PATENT DOCUMENTS 1165075  9/1969  United Kingdom .

*Primary Examiner*—Helen M. S. Sneed
*Attorney, Agent, or Firm*—Browdy and Neimark

[57] ABSTRACT

Complexes of pentaerythritol derivatives such as sulfuric acid ester of pentaerythritol or dipentaerythritol with a basic polyaluminum chloride and process for preparing the same are disclosed. The complex is novel and has a good anti-pepsin activity and therefore it is useful as an anti-ulcer agent.

The complex is prepared by reacting pentaerythritol or dipentaerythritol with a sulfating agent and then reacting the resulting sulfate with a basic polyaluminum chloride.

6 Claims, 1 Drawing Figure

PENTAERYTHRITOL DERIVATIVE

FIELD OF THE INVENTION

This invention relates to a complex of pentaerythritol derivative such as sulfuric acid ester of pentaerythritol or dipentaerythritol with a polyaluminum chloride.

The complex of this invention is novel and has a good anti-pepsin activity and therefore it is useful as an anti-ulcer agent.

SUMMARY OF THE INVENTION

According to this invention, the complex is prepared by reacting pentaerythritol or dipentaerythritol with a sulfating agent such as sulfuric acid, sulfuric anhydride, chlorosulfonic acid, pyridine-sulfuric anhydride complex or the like, and then reacting the resulting sulfuric acid ester with a basic polyaluminium chloride. The sulfation reaction is conducted in the presence of a base such as pyridine, N,N-dimethylformamide and the like usually at 20°–160° C., preferably 70°–100° C., for 1–3 hours. The reaction of the sulfuric acid ester with a basic polyaluminum chloride is conducted in an aqueous medium using usually 1–5 molecules, preferably 2–3.5 molecules, of the basic polyaluminum chloride per one sulfate radical. The basic polyaluminum chloride which can be used in this invention involves polymers having a basicity of from 0.67 to 0.83 and prepared by reacting metallic aluminum with aluminum chloride in an aqueous medium.

The complex prepared as described above contains 4–11% of sulfur, 9–22% of aluminum and has a moler ratio of sulfur to aluminum (S/Al) in the range from 2.0 to 3.4. The molecular weights of dipentaerythritol sulfuric acid ester/polyaluminum hydroxide complex and pentaerythritol sulfuric acid ester/polyaluminum hydroxide complex are 1500–3000 and 1000–1900, respectively. The complex of this invention essentially consists of sulfuric acid esters of primary hydroxy radicals and does not contain the esters of secondary hydroxy radicals. It is therefore so stable that desulfation reaction by hydrolysis is hardly caused at all even in a suspension in water. In addition, the complex easily provides a soft oily slurry by the addition of water and therefore it can uniformly cover the ulcer-affected part of a gastric wall even in the absence of an acid or gastric juice so that such part is protected from the attack of pepsin.

Accordingly, when administered to a patient, the complex of this invention is used as it is or is formulated into an oily slurry or a suspension in water with the aid of a surfactant. If the complex is administered in a suspension, it is desirably dispersed in the stomach so that the therapeutic effects on the ulcer or inflammation of the lower part of the esophagus or cardiac part of the stomach can be improved.

DETAILED DESCRIPTION OF THE INVENTION

EXPERIMENT 1

Figure 1:
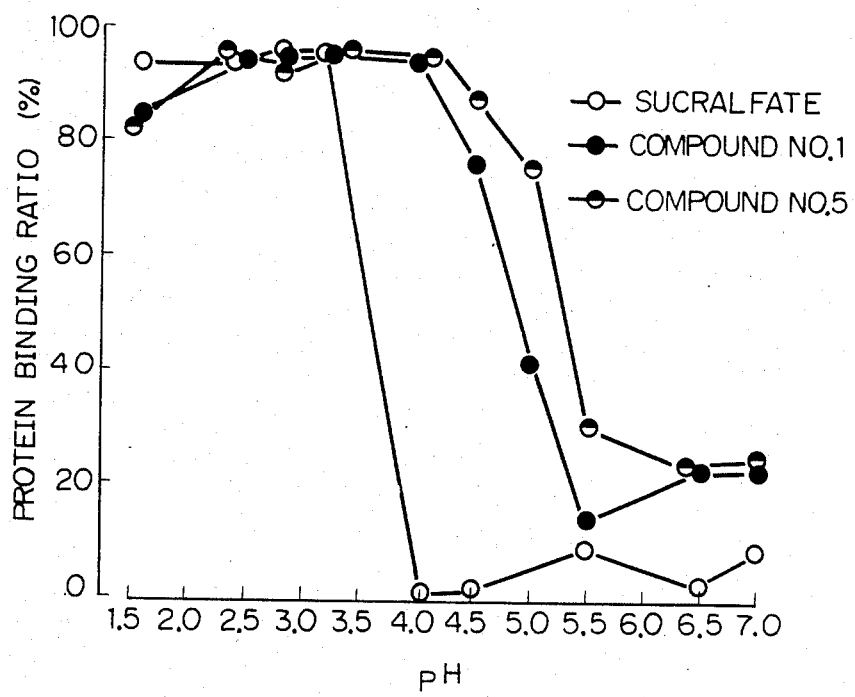
FIG. 1 is a graph showing the test results of Experiment 2 below. In the FIG. 1, protein binding ratios of the compounds of this invention and Sucralfate (control) at various pH are plotted.

Determination of binding ratio of the complexes to protein:

A test complex was added in an amount of 2 mg or 10 mg to 5 ml of a solution of bovine serum albumin in a Clark-Lubs buffer (pH 1.6) at a concentration of 1 mg of albumin per 5 ml of the buffer. After incubation of the mixture at 37° C. for 20 minutes under shaking, the mixture was centrifuged at 3,000 r.p.m. for 10 minutes. Aliquots of the supernatant were analyzed calorimetrically for protein using the method of Lowry. That is, to 0.5 ml of the supernatant was added 2 ml of the mixed solution which had been prepared by mixing 50 ml of a 0.1N NaOH solution containing 2% $Na_2CO_3$ with 1 ml of a solution of copper sulfate (0.5 g) and sodium tartarate (1 g) in distilled water (100 ml), and then 0.2 ml of the phenol test reagent diluted to twice the original volume. The mixture was then allowed to stand for 30 minutes and the extinction of the blue-colored solution was determined at 750 nm.

TABLE 1

| Test Compound | Binding Ratio to Protein | |
|---|---|---|
| | 2 mg | 10 mg |
| 1 | 77.3% | 97.1% |
| 2 | 74.2% | 87.5% |
| 3 | 78.1% | 95.2% |
| 4 | 77.3% | 97.1% |
| 5 | 0.0% | 96.2% |
| 6 | 0.0% | 56.7% |
| 7 | 2.3% | 72.1% |
| 8 | 79.7% | 91.3% |

The results are shown in Table 1. The numbers given to the test compounds correspond to those of the Examples described hereunder.

EXPERIMENT 2

Determination of binding ratio to protein at various pH:

The test complex (5 mg) was added to 5 ml of a solution which had been prepared by dissolving 1 mg of bovine serum albumin per 5 ml of a buffer having a different pH as shown in FIG. 1. After incubation at 37° C. for 20 minutes while shaking, the mixture was centrifuged at 3,000 r.p.m. for 10 minutes and the supernatant (0.5 ml) was analyzed for protein using the method of Lowry described in Experiment 1.

The binding ratio in each of the test complexes was calculated on the basis of the control wherein the protein quantity of a sample containing no test complex is deemed as 100.

The results are shown in FIG. 1. The numbers defining the test compounds correspond to those of the Examples described hereunder.

EXPERIMENT 3

Determination of anti-pepsin activity:

As a substrate, bovine serum albumin was dissolved in a Clark-Lubs buffer (pH 1.6) at a concentration of 12, 24, 48 or 96 mM. Separately, a test complex was dissolved in 1N HCl at a concentration of 500 or 1500 μM and the pH was adjusted to 1.6. The substrate solution (2 ml) was mixed with the test solution (2 ml) and the mixture was subjected to preincubation at 37° C. for 10 minutes, and to the preincubated mixture was added 1 ml of a pepsin solution in the Clark-Lubs buffer at a concentration of 25 μg/ml. The mixture was then incubated at 37° C. for 20 minutes while shaking.

After centrifugation, 5 ml of 10% TCA was added to the supernatant (0.5 ml) and the mixture was allowed to stand at room temperature for 10 minutes. After centrifugation, the tyrosine quantity in the supernatant was determined by the Anson method. The Anson method was conducted by adding to 0.5 ml of the supernatant, 2.5 ml of 0.3N aqueous NaOH and 0.5 ml of the phenol reagent diluted to three times the original volume with distilled water, and then the mixture was allowed to stand at room temperature for 30 minutes. The optical absorption thereof was determined at 640 nm.

The results are shown in Table 2 below.

TABLE 2

| Test Compound | Concentration (μM) | BSA conc. (μM) 12 | BSA conc. (μM) 96 |
|---|---|---|---|
| 1 | 496 | 91.0 | 21.5 |
| 2 | " | 89.1 | 16.6 |
| 3 | " | 91.0 | 18.3 |
| 4 | " | 91.0 | 16.0 |
| 1 | 1489 | 91.8 | 77.7 |
| 2 | " | 89.9 | 76.6 |
| 3 | " | 87.2 | 83.7 |
| 4 | " | 89.9 | 78.5 |
| 5 | 496 | 46.3 | 19.8 |
| 6 | " | 49.1 | 3.8 |
| 7 | " | 71.9 | 4.7 |
| 8 | " | 78.2 | 4.7 |
| 5 | 1489 | 84.5 | 15.1 |
| 6 | " | 83.6 | 13.8 |
| 7 | " | 86.4 | 19.1 |
| 8 | " | 84.5 | 21.5 |

EXPERIMENT 4

Anti-ulcer activity on Shay rats:

Male SD rats (180–200 g) were deprived of food for 48 hours and had free access to water. Under ether anesthesia the abdomen of each rat was incised and the pylorus ligated. Concurrently the test complex was orally administered and the abdomen was closed. The animals were killed 16 hours later by an overdose, and the stomach of each rat removed. The stomach was incised along the greater curvature and examined for gastric ulcers developed in the forestomach. The damaged mucosa in shay ulcers was measured under a dissecting microscope (x10) with a square grid, summed, and arbitrarily classified into 5 degrees by an erosion index.

The results are shown in Table 3.

TABLE 3

| Test Compound | Dose (mg/kg) | Erosion Index (mean ± SE) | Nos. of Animals | Percent Inhibition (%) |
|---|---|---|---|---|
| Na salt* | 300 | 1.4 ± 0.2** | 5 | 58.8 |
| 3 | 300 | 0.6 ± 0.4** | 5 | 82.4 |
| Control | (H$_2$O) | 3.4 ± 0.4 | 5 | — |

*Sodium salt of sulfuric acid ester of dipentaerythritol
**p < 0.01

EXAMPLE 1

(a) Preparation of basic polyaluminum chloride

Metallic aluminum particles (3.35 g) were added to a solution of aluminium chloride hexahydrate (10 g) in distilled water (45 ml) charged in a vessel equipped with a condenser, and the mixture was heated on a steam bath whereby the reaction proceeded while vigorously generating hydrogen gas. After completion of dissolving the metallic aluminum, the reaction mixture was cooled, and filtered to remove all of a small amount of the resulting precipitates to give 49 ml of a colorless, clear aqueous solution of polyaluminum chloride. The product had a basicity of 0.75.

(b) A suspension of dipentaerythritol (10 g) in dried pyridine (200 ml) was heated at 80° to 90° C. To the suspension was added the sulfuric anhydride-pyridine complex (50 g) which had been prepared from sulfuric anhydride and pyridine, and the reaction was continued at that temperature for 2.5 hours. After cooling, the resulting oily pyridinium salt of sulfuric acid ester was separated from the pyridine layer. The oily product (100 ml) was dissolved in 100 ml of distilled water and neutralized with a 10% NaOH aqueous solution to adjust a pH to 8, while coolign with ice. The solution was then concentrated under reduced pressure into a volume of about 50 ml, neutralized again with a 10% NaOH aqueous solution to pH 8, and concentrated under reduced pressured into about 30 ml in volume. After adding 100 ml of ethanol, the mixture was stirred vigorously and the resulting white precipitates were recovered by filtration to give a crude complex of sodium salt of dipentaerythritol hexasulfuric acid ester. The crude product was purified by dissolving it in distilled water in an amount ten times the volume of the product and adding to the solution ethanol of 30 times the volume of the solution.

Calculated for $C_{10}H_{16}O_7(SO_3Na)_6 \cdot 4H_2O$: S=20.51%; Found: S=20.33%.

(c) Sodium salt of dipentaerythritol hexasulfuric acid ester (3 g) was dissolved in distilled water while vigorously stirring, and to the resulting solution was added basic polyaluminum chloride obtained in above (a) in such an amount as 3–3.5 molecules in terms of aluminum per a sulfate radical. The resulting oily product was recovered by decantation and washed several times with water. Methanol (50 ml) was added to the oily product and the mixture was vigorously agitated to give white powdery solid which was recovered by filtration, washed with methanol and dried at room temperature under reduced pressure for several hours to give the aluminum complex (Compound 2).

By the similar method, various polyaluminium chlorides shown in Table 4 below each of which had a different basicity, were prepared.

TABLE 4

| Test Compound | Basicity | Yield (g) | Elemental Analysis (%) C | H | S | Al | Al/S Molar Ratio |
|---|---|---|---|---|---|---|---|
| 1 | 0.67 | 6.72 | 4.61 | 3.49 | 8.48 | 18.1 | 2.54 |
| 2 | 0.75 | 5.53 | 4.75 | 3.57 | 8.90 | 19.2 | 2.57 |
| 3 | 0.80 | 6.39 | 4.62 | 3.34 | 8.68 | 19.9 | 2.73 |
| 4 | 0.83 | 6.38 | 4.20 | 3.41 | 7.80 | 20.6 | 3.14 |

EXAMPLE 2

A suspension of pentaerythritol (5 g) in pyridine (100 ml) was heated at 80° to 90° C. and a sulfuric anhydridepyridine complex (30 g) was added to the suspension. The mixture was then treated as in Example 1 to give 23.6 g of sodium salt of pentaerythritol tetrasulfuric acid ester.

Calculated for $C_5H_8O_4(SO_3Na)_4 \cdot 3H_2O$: S=21.44%; Found: S=21.64%.

The product obtained above (3 g) was dissolved in 30 ml of distilled water and basic polyaluminum chloride was added to the solution as in Example 1 while vigorously stirring. The reaction mixture was treated as in Example 1 to give compounds as shown in Table 5 below.

TABLE 5

| Test Compound | Basicity | Yield (g) | Element analysis (%) | | | | Al/S Molar Ratio |
|---|---|---|---|---|---|---|---|
| | | | C | H | S | Al | |
| 5 | 0.67 | 6.09 | 3.50 | 3.69 | 7.14 | 18.8 | 3.13 |
| 6 | 0.75 | 5.70 | 3.43 | 3.33 | 8.21 | 20.4 | 2.96 |
| 7 | 0.80 | 5.04 | 3.55 | 3.35 | 8.78 | 20.4 | 2.76 |
| 8 | 0.83 | 6.37 | 3.44 | 3.36 | 8.27 | 20.7 | 2.98 |

What is claimed is:

1. A complex of pentaerythritol sulfuric acid ester/polyaluminum hydroxide, or of dipentaerythritol sulfuric acid ester/polyaluminium hydroxide.
2. A complex according to claim 1 wherein said complex contains 4–11% of sulfur and 9–22% of aluminum.
3. A complex according to claim 1 wherein the molar ratio of sulfur to aluminum (S/Al) is in the range from 2 to 3.5.
4. A complex according to claim 1 wherein said complex is pentaerythritol sulfuric acid ester/polyaluminum hydroxide complex having a molecular weight in the range from 1000 to 1900.
5. A complex according to claim 1 wherein said complex is dipentaerythritol sulfuric acid ester/polyaluminum hydroxide complex having a molecular weight in the range from 1500 to 3000.
6. A complex according to claim 1 wherein said complex is in an oily or powdery state.

* * * * *